United States Patent [19]

Shibahashi et al.

[11] Patent Number: 4,920,991

[45] Date of Patent: May 1, 1990

[54] THERMOCHROMIC ARTIFICIAL NAIL

[75] Inventors: Yutaka Shibahashi; Norikazu Nakasuji, both of Aichi, Japan

[73] Assignee: Pilot Ink Co., Ltd., Aichi, Japan

[21] Appl. No.: 274,254

[22] Filed: Nov. 21, 1988

[30] Foreign Application Priority Data

Nov. 20, 1987 [JP] Japan .................................. 62-177731

[51] Int. Cl.$^5$ ............................................. A45D 29/00
[52] U.S. Cl. .......................................... 132/73; 63/32; 128/736; 40/448
[58] Field of Search .................... 132/73; 128/736; 40/448, 442; 283/81; 428/1; 63/32, DIG. 1; 350/351

[56] References Cited

U.S. PATENT DOCUMENTS

| 2,816,555 | 12/1957 | Klump | 132/73 |
| 3,802,945 | 4/1974 | James | 40/448 |
| 3,951,133 | 4/1976 | Reese | 128/736 |
| 4,022,706 | 5/1977 | Davis | 350/351 |
| 4,028,118 | 6/1977 | Nakasuji et al. | |
| 4,142,782 | 3/1979 | O'Brian | 40/442 |
| 4,220,016 | 9/1980 | Frenger | 63/32 |
| 4,720,301 | 1/1988 | Kito et al. | |

Primary Examiner—James R. Brittain
Assistant Examiner—J. Hakomaki
Attorney, Agent, or Firm—Sughrue, Mion, Zinn, Macpeak & Seas

[57] ABSTRACT

Disclosed is a thermochromic artificial nail comprising an artificial nail having provided thereon a thermochromic layer, which comprises a thermochromic material changeable in visible external color in response to a change in temperature, wherein said thermochromic layer has a thickness of at least 1 μm.

10 Claims, 1 Drawing Sheet

THERMOCHROMIC ARTIFICIAL NAIL

FIELD OF THE INVENTION

The present invention relates to a thermochromic artificial nail, and particularly relates to a thermochromic artificial nail constructed to change in response to a change in temperature so as to exhibit various changeable external appearances.

BACKGROUND OF THE INVENTION

A number of proposals for artificial nails have been provided. The proposals include an artificial nail of the type made of a suitably-shaped sheet material, nail-shaped plastics, a metal piece, or the like, and arranged so as to be attachable to the surface of a natural nail through a pressure-sensitive adhesive layer provided on the rear surface of the, artificial nail. The proposals also include an artificial nail of the type provided with a recess portion into which a top end of a natural nail can be inserted so that the artificial nail can be removably fitted to the natural nail. In some of those proposals, a pattern, a colored layer, or the like is provided on the surface of the artificial nail as ornamentation. (Japanese Utility Model Unexamined Publication Nos. 53-64660 and 59-117410, etc.)

However, even if additionally provided with such ornamentation, the conventional artificial nail's external visual appearance can be recognized only in one set appearance, and has no mystery of change because its visible external appearance is not variable.

SUMMARY OF THE INVENTION

The present invention is intended to provide a novel artificial nail having an external appearance which can be reversibly or quasi-reversibly changed in response to a change in temperature so that the novel artificial nail is rich in the mystery of change, tastefulness, ornamentation power, and variety, to thereby further improve the value of the artificial nail of the kind described above.

To this end the present invention provides a thermochromic artificial nail comprising an artificial nail having provided thereon a layer, which comprises a thermochromic material changeable in visible external color in response to a change in temperature, wherein said thermochromic layer has a thickness of at least 1 μm.

DETAILED DESCRIPTION OF THE INVENTION

Figure 1:
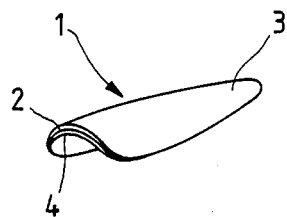
FIG. 1 is a perspective view of the thermochromic artificial nail according to the present invention.
Figure 2:
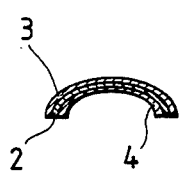
FIG. 2 is a sectional view of the same.
Figure 3:
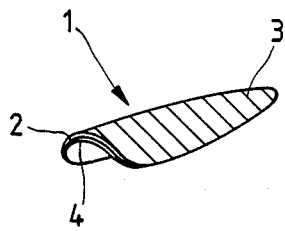
FIG. 3 is a perspective view showing the state in which the color of the artificial nail of FIG. 1 has changed into another color.

Referring to the drawings, the present invention will be described hereinafter.

Basically, the thermochromic artificial nail is constructed as follows. A thermochromic layer 3, which is changeable in color in response to a temperature within a range of living temperatures (generally from $-10°$ C. to $+40°$ C.), is formed on a surface of an artificial nail 2, so that the thermochromic layer can change in color in response to a change in temperature so as to exhibit various external visual appearances.

In the above description, the basic artificial nail 2 may be of one of the conventionally known various types, such as the type made of a suitably-shaped sheet material, nail-shaped plastics, a metal piece, or the like, and arranged so as to be attachable to a surface of a natural nail through a pressure-sensitive adhesive layer provided on the rear surface of the artificial nail. The basic artificial nail 2 may also be of the type provided with a recess portion into which a top end of a natural nail can be inserted so that the artificial nail can be removably fitted to the natural nail. Other types are possible.

The thermochromic layer 3 may be provided on a portion of or on the whole of the surface of the artificial nail 2. In the case of the artificial nail 2 made of thermoplastics resin, or the like, the artificial nail may be moldings of the thermoplastics resin or the like in which a thermochromic pigment is integrally blended.

The thermochromic layer 3 may be formed of conventionally known reversible or of conventionally known quasi-reversible thermochromic material.

The thermochromic layer 3 has a thickness of 1 μm or more so that a change in color is clearly recognizable through a visual sense.

As the reversible thermochromic material, it is effective to use a conventionally known material containing, for example. (I) a thermochromic pigment composed of three components; (x) an electron donor coloring organic compound. (y) a developer for developing the coloring organic compound, and (z) a coloring temperature modifier for determining a temperature and thereupon generating a coloring reaction between the coloring organic compound and the developer; (II) a reversible thermochromic pigment in the form of fine particles of resin solid solution of the above three components (x, y and z); or the like. As a preferable example, it is possible to utilize the thermochromic material disclosed in U.S. Pat. No. 4,028,118 previously filed by the inventors of this application, incorporated herein by reference.

In the system using the above-mentioned reversible thermochromic material, the color is reversibly changed at a predetermined temperature (color-changing point) as a boundary, so that the nail's surface exhibits one external appearance when the material is at a temperature higher than the predetermined temperature which is selected as the color-changing point, and the nail's surface exhibits a noticeably different external appearance when the material is at a temperature lower than the selected color-changing point.

As the quasi-reversible thermochromic material, it is possible to utilize the reversible thermochromic recording composition in U.S. Pat. No. 4,720,301, also incorporated herein by reference, previously filed by the inventors of this application. The above-mentioned quasi-reversible thermochromic coloring material is a homogeneous compatible material composed of three components, that is, (a) an electron donor coloring organic compound, (b) an electron acceptor compound, and (c) a compound which will act as a medium for quasi-reversibly causing a coloring reaction between the components (a) and (b). This reaction results in the exhibition of a so-called "hysteresis characteristic", which is described below.

Figure 4:
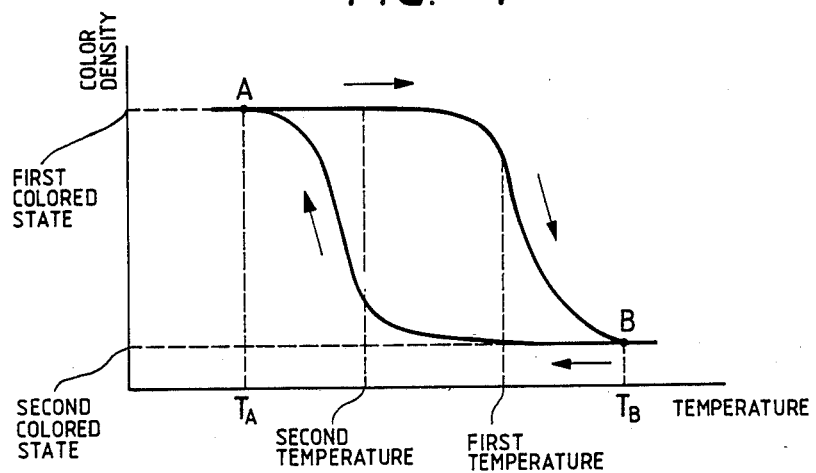
FIG. 4 is a graph useful in explaining the present invention by showing a hysteresis characteristic of a quasi-reversible thermochromic material.

The meaning of the above-mentioned hysteresis characteristic is as follows. The shape of the curve obtained by plotting the color density as a function of temperature depends on whether the temperature is changing from below to above the range of a predetermined color changing temperature, or from above to below the same range. Therefore, the curves in the foregoing two cases form a loop when they are combined as shown in FIG. 4. Assuming that the temperatures at the junctions between the two curves at the opposite ends of the loop at the lower and higher sides are represented by $T_A$ and $T_B$ respectively, the quasi-reversible thermochromic coloring used according to the present invention is characterized as follows.

The lower temperature $T_A$ is a relatively low temperature with respect to the range of temperatures common in the human environment. For example, it can be produced by ice or cold water, that is, a temperature within a range of from about $-5°$ C. to about $15°$ C. The higher temperature $T_B$ is a relatively high temperature with respect to the range of temperatures common in the human environment. For example, it can be produced by the human body, a hot water bath, a hair drier, or the like. That is, the higher temperature $T_B$ is within a range of from about $27°$ C. to about $90°$ C., preferably from $30°$ C. to $50°$ C. With this quasi-reversible thermochromic coloring, the range of temperature in which both a first color state and a second color state can co-exist extends over the range of temperatures common in the human environment. This range will hereinafter be referred to as the "two-color holding temperature range" or as "$T_A$-$T_B$". Preferably the two-color holding temperature range exists within the range of about $-5°$ C. to about $90°$ C., more preferably from about $10°$ C. to about $35°$ C. It should be noted that one of the first or second color states (but not both in the same embodiment) can actually be colorless.

By use of such a coloring material providing the above-mentioned characteristic, not only can the color (appearance) of the surface of the thermochromic layer 3 be changed in response to a change in temperature, but the coloring material can provide a double-state characteristic in which either one of the two selectable appearances can be desiredly selected so as to maintain the selected appearance within the two-color holding temperature range. This phenomenon will be explained in detail later on in the specification.

The thermochromic layer 3 can be formed in either of two ways. The thermochromatic layer 3 can be formed as a coating layer on the surface of the artificial nail 2. In this case a thermochromic pigment, i.e., coloring material, in the form of ink, colors, paint, or the like, is dispersed in a suitable vehicle including a binder and then coated on the artificial nail 2 to form the thermochromic layer 3.

In the alternative, the artificial nail 2 can be formed of a material in which the above-mentioned thermochromic pigment or coloring material is blended with and dissolved in a thermoplastic resin so that the thermochromic layer 3 and the artificial nail 2 are essentially one and the same.

In the above description, the thermochromic material can be formed of microcapsules each containing the thermochromic pigment or coloring material. In this case the microcapsules have grain size of about 0.5–50 $\mu$m, and are effective from the standpoint of dispersion workability, strength, sensitivity, etc.

A thermo-setting resin or thermoplastic resin can be used as the binder, and either one of the thermosetting resin and thermoplastic resin is selected to suitably correspond to the quality of the material of the artificial nail.

The thickness of the coating layer is within a range of from about 1 $\mu$m to 400 $\mu$m, preferably within a range of from 5 $\mu$m to 200 $\mu$m, more preferably within the range of 10 $\mu$m to 200 $\mu$m, and the color-changing effect can be satisfied within the former range. If the thickness is less than 1 $\mu$m, the color-change lacks distinctness, but if it exceeds 400 $\mu$m, the beauty in external appearance is apt to deteriorate.

In the case of where the thermochromic material contained in microcapsules, the amount of thermochromic material-containing microcapsules in the thermochromic layer is within a range of from 5 to 80 weight %, preferably within a range of from 10 to 60 weight %, in order to achieve a satisfactory thermochromic effect.

That is, if the rate of the thermochromic material in the thermochromic layer is selected to be less than 5 weight %, the coloring density is so low that the color-change cannot be clearly recognized through a visual sense, while if the rate exceeds 80 weight %, it becomes difficult to recognize a clear color-disappearing state through a visual sense.

The thermochromic layer 3 may be formed not only as a layer which changes in color equally all over its entire surface, but as a layer having thermochromic patterns thereon so that the color-changing can be effected with more variety. That is, the thermochromic layer may be formed as a layer having a plurality of thermochromic areas, which differ from one another in thermochromic response to temperature. Such thermochromic areas may be formed side by side to form patterns and may include non-thermochromic areas, i.e., a layer colored with a generally-used non-color-changing pigment or the like. In other words, a thermochromic layer could have areas of the thermochromic layer that will change color in response to change in temperature, while having other areas which will not change color (regardless of temperature change).

In the system in which the thermochromic layer 3 is formed of the reversible thermochromic coloring material, the color is changed in response to a change in temperature with respect to a color-changing point as a boundary so that when the temperature is higher than the color-changing point, the external appearance of the layer 3 is different as compared with the external appearance of layer 3 when the temperature is lower than the color-changing point. Thus, the appearance can be reversibly brought back and forth into and out of the initial appearance in response to change in temperature across the color-changing point.

In the system in which the thermochromic layer 3 is formed of the quasi-reversible thermochromic coloring material, not only does the layer 3 color change in response to a change in temperature, but by virtue of the aforementioned hysteresis characteristic, the artificial nail's user can select either (a) the color which is exhibited at a temperature lower than the color-changing point, or (b) the color which is exhibited at a temperature higher than the color-changing point, and then the user can keep the selected color constant within a certain range of temperature common to the human environment. This point will be described below in more detail through a hypothetical illustration.

For illustrative purposes it will be assumed that the thermochromic layer 3, which is coated with the quasi-reversible thermochromic color, is in a colored state (first state) below temperature $T_A$ and is in a colorless state (second state) above temperature $T_B$, the range $T_A$-$T_B$ being common to the human environment.

The hypothetical situation will start with the thermochromic layer 3 in the colorless second state at a given temperature ($T_G$) within the range of $T_A$ to $T_B$, so that the color of artificial layer 2 (substrate) appears from beneath the colorless thermochromic layer 3. Next, the surface of this now colorless thermochromic layer 3 is cooled below the above-mentioned temperature $T_A$ so as to change the thermochromic layer 3 to the colored state. Then, the temperature of the thermochromic layer 3 is returned to the original given temperature ($T_G$), but the color of the low temperature colored state (first state) is nevertheless held constant within the range of $T_A$-$T_B$ due to the hysteresis characteristic.

On the other hand, if the temperature of the surface of the same thermochromic layer is now heated above the above-mentioned temperature $T_B$ so as to change the thermochromic layer back to the colorless state and then returned to the original given temperature ($T_G$), the higher temperature colorless state is held constant within the range of $T_A$-$T_B$ despite the fact that the thermochromic layer would appear colored within this range if the layer had been warmed from below $T_A$ instead of being cooled from above $T_B$. The same explanation applies to the interchangeability between the respective appearances of switchable first and second colors.

Thus, the nail of the present invention is constructed such that one of two visual appearances can be selected and held constant between $T_A$ and $T_B$ according to user's desire. The selected configuration can be further varied into the other configuration at will (by either cooling below $T_A$ or heating above $T_B$), and the thus-obtained alternative appearance remains stable between $T_A$ and $T_B$.

The present invention will hereinafter be illustrated by examples but is not to be construed as being limited thereto.

EXAMPLE 1

Paint containing a pearl-gray pigment was applied onto the surface of an artificial nail 2 so as to form a non-color-changing layer colored in pearl-gray, and then the layer was further coated with paint (A) including a reversible thermochromic pigment having a color-changing point at about 20° C. so that a pink color was visible at a temperature not higher than the color-changing point while the pink color disappeared at a temperature not lower than the color-changing point, thereby obtaining a thermochromic artificial nail 1 provided with a thermochromic layer 3 having a thickness of about 50 μm. (The artificial nail 2 may be of the sheet-like adhesion type or of the type molded in the form of a nail. That applies to the following examples.) An adhesive layer 4 was provided on the rear surface of the artificial nail 1 so as to put the artificial nail into practical use.

Paint (A) -- 6 weight portions of a thermochromic pigment of microcapsules each being formed of including a thermochromic composition solidified to its inside with an acrylic-resin/amine curing agent and each having a grain size of 5-10 μm, and 20 weight portions of epoxy resin of the glycidyl ether type, and 8 weight portions of an amine curing agent were mixed with each other to thereby obtain the paint (A).

The artificial nail 1 looked pink at its external appearance at a temperature not higher than 20° C. while the external appearance was recognized to be pearl-gray through a visual sense at a temperature above 20° C. The change in appearance was reversible in accordance with changes in temperature.

EXAMPLE 2

The thermochromic artificial nail 1 was formed with a material in which a pearl-gray pigment and a reversible thermochromic pigment (the same as that used in Example 1) were blended with and dissolved in polypropylene resin. The thermochromic artificial nail was formed to have a recess portion into which a top end of a natural nail could be inserted and a plane portion of about 0.4 mm in thickness. [It is effective to select the additive ratio of the reversible thermochromic pigment to be within a range of from 1 to 15 weight % relative to the entire weight.]

The artificial nail 1 exhibited an appearance similar to those in Example 1 in accordance with changes in temperature.

EXAMPLE 3

Patterns were disposed on the surface of an artificial nail 2 with light-blue/orange color non-color-changing ink to form a colored layer and then the upper surface of the colored layer was coated with the reversible thermochromic paint used in Example 1 so as to cover the colored layer to thereby constitute a thermochromic artificial nail 1 provided with a thermochromic layer 3 having a thickness of about 100 μm.

The artificial nail 1 had an external appearance which was recognized to be pink through a visual sense within a temperature range not higher than 20° C., while recognized so that the pink color disappeared and the light-blue/orange patterns became visible within a temperature range not lower than 20° C. The change in external appearance was observed reversibly in accordance with changes in temperature.

EXAMPLE 4

Paint (B) containing a quasi-reversible thermochromic coloring material reversibly changeable between pearl-gray and pink color (the point $T_A$: 10° C., the point $T_B$: 32° C.) was prepared, and then the surface of an artificial nail 2 was coated with the thus prepared paint (B) and dried to thereby constitute a thermochromic artificial nail 1 provided with a thermochromic layer 3.

The paint (B) was obtained by uniformly mixing: 8 weight portions of a pigment of microcapsules each containing the quasi-reversible thermochromic coloring material and each having a grain size of 5-10 μm; 50 weight portions of acrylic resin (a solvent in a group of xylene/butyl acetate, solid content of about 50%); and a dilution solvent (30 weight portions of xylene and 20 weight portions of toluene).

EXAMPLE 5

A thermochromic artificial nail 1 was constituted in the same manner as in Example 2 except that the quasi-reversible thermochromic coloring material of Example 4 was used in place of the reversible thermochromic pigment of the Example 2.

EXAMPLE 6

A thermochromic artificial nail 1 was constituted in the same manner as in Example 3 except that the quasi-reversible thermochromic coloring material of Example 4 was used in place of the reversible thermochromic pigment of Example 3. In the respective nails 1 in Examples 4, 5, and 6, the pink color disappeared so that the pearl external appearance (in Examples 4 and 5) and the light-blue/orange patterns (in Example 6) were recognized through a visual sense, in a range of temperatures above 32° C. (the open air temperature, warm water, warm wind, frictional heat, human breath, etc.). The respective external appearances maintaining the above-mentioned appearances were recognized through a visual sense in a range of temperatures of from 10° C. to 32° C. When the artificial nail was cooled below 10° C., the pink color was recovered so that the external appearance of the pink color was recognized through a visual sense.

The change in the external appearance in accordance with changes in temperature as described above could be made to reappear repeatedly.

The artificial nail of the present invention has a constitution in which a thermochromic layer 3 is provided on an artificial nail 2 so that the artificial nail changes in color in response to changes in temperature about a predetermined temperature as a boundary so as to make its external appearance vary with temperature. Thus, it is possible to provide a novel artificial nail in which unexpectedness in change, ornamentation power, tastefulness, etc. are additionally provided.

Particularly in the system in which the thermochromic layer 3 is formed of a quasi-reversible thermochromic coloring material, not only does the color of the surface change in accordance with changes in temperature, but either one of the appearances before and after a change can be desiredly selected by a user and be held constant at a temperature within a range common to the human environment, so that one kind of artificial nail can provide ornamentation power as well as utility as an artificial nail having variable external appearances.

While the invention has been described in detail and with reference to specific embodiments thereof, it will be apparent to one skilled in the art that various changes and modifications can be made therein without departing from the spirit and scope thereof.

What is claimed is:

1. A thermochromic artificial nail comprising an artificial nail having provided thereon a thermochromic layer of a thickness of at least 1 μm, said thermochromic layer comprising a thermochromic material changeable in visible external appearance in response to a change in temperature, wherein said thermochromic material is formed of microcapsules each having a grain size of about 0.5–50 μm and containing a quasi-reversible thermochromic coloring material which exhibits a hystersis characteristic in accordance with the change in temperature so as to exhibit interchangeability between a first color state and a second color state, where one of said first and second color states can be colorless, wherein a two-color holding temperature range is set within a temperature range common to the human environment, and wherein said microcapsules are fixed in a binder in a dispersed state so as to form said thermochromic layer, whereby the color of said thermochromic layer is changed by heating or cooling said layer so as to change the visible external appearances and one of the visible external appearances is selectively maintained in said temperature range.

2. A thermochromic artificial nail according to claim 1, in which thermochromic layer is a coating layer formed of said thermochromic material and a binder.

3. A thermochromic artificial nail according to claim 1, in which said artificial nail is made of thermoplastic resin.

4. A thermochromic artificial nail according to claim 1, in which said two-color holding temperature range of said quasi-reversible thermochromic coloring material is within a range of from about −5° C. to 90° C.

5. A thermochromic artificial nail according to claim 4, in which said two-color-holding temperature range of said quasi-reversible thermochromic coloring material is within a range of from about 10° C. to 35° C.

6. A thermochromic artificial nail according to claim 2, in which said thermochromic material is formed of microcapsules each containing a reversible or quasi-reversible thermochromic coloring material, said microcapsules being fixed to a binder in a dispersed state so as to form said coating layer, said microcapsules being 5–80 weight % of said coating layer.

7. A thermochromic artificial nail according to claim 6, wherein said microcapsules are present in the thermochromic layer within a range of from 10 to 60 weight % of said coating layer.

8. A thermochromic artificial nail according to claim 2, in which the thickness of said coating layer is about 1–400 μm.

9. A thermochromic artificial nail according to claim 8, in which the thickness of said coating layer is about 5–200 μm.

10. A thermochromic artificial nail according to claim 9, in which the thickness of said coating layer is about 10–200 μm.

* * * * *